(12) United States Patent
Usowicz et al.

(10) Patent No.: US 7,951,597 B2
(45) Date of Patent: May 31, 2011

(54) PRESSURIZED FLUID SAMPLE INJECTOR AND METHOD OF INJECTING FLUID SAMPLES

(75) Inventors: James E. Usowicz, Webster, MA (US); Theodore C. Ciolkosz, Milton, MA (US); Russell Keene, Sudbury, MA (US); Daniel J. McCormick, Westford, MA (US)

(73) Assignee: Waters Technologies Corporation, Milford, MA (US)

( * ) Notice: Subject to any disclaimer, the term of this patent is extended or adjusted under 35 U.S.C. 154(b) by 599 days.

(21) Appl. No.: 11/532,234

(22) Filed: Sep. 15, 2006

(65) Prior Publication Data

US 2007/0062875 A1  Mar. 22, 2007

Related U.S. Application Data

(63) Continuation-in-part of application No. 11/072,906, filed on Mar. 4, 2005, now abandoned, which is a continuation of application No. PCT/US03/28249, filed on Sep. 10, 2003.

(60) Provisional application No. 60/409,836, filed on Sep. 11, 2002.

(51) Int. Cl.
   G01N 1/10       (2006.01)
   G01N 35/10      (2006.01)

(52) U.S. Cl. ..... 436/43; 73/61.56; 73/64.56; 73/863.83; 73/864.21; 73/864.83; 422/67; 422/501; 422/522; 422/546; 422/70; 436/54; 436/161; 436/180

(58) Field of Classification Search ............ 210/90, 210/101, 198.2, 635, 656, 741; 73/61.55, 73/61.56, 64.56, 863.01, 863.02, 863.72, 863.73, 864.21, 864.22, 864.83, 863.83; 422/63, 68.1, 70, 67, 100, 103, 501, 521, 522, 546; 436/161, 174, 180, 43, 54

See application file for complete search history.

(56) References Cited

U.S. PATENT DOCUMENTS

| | | | |
|---|---|---|---|
| 3,775,058 A | | 11/1973 | Bush |
| 3,918,913 A | | 11/1975 | Stevenson et al. |
| 3,988,921 A | | 11/1976 | Lightner |
| 3,999,439 A | * | 12/1976 | Munk ................. 73/864.83 |
| 4,116,046 A | | 9/1978 | Stein |
| 4,242,909 A | * | 1/1981 | Gundelfinger ......... 73/864.21 |
| 4,457,846 A | | 7/1984 | Munk |
| 4,464,940 A | | 8/1984 | Pospisil |
| 4,533,643 A | * | 8/1985 | Bell et al. .............. 436/178 |
| 4,674,323 A | | 6/1987 | Rulf et al. |
| 4,756,201 A | | 7/1988 | Uffenheimer et al. |
| 4,835,109 A | | 5/1989 | Trisciani et al. |
| 4,836,038 A | | 6/1989 | Baldwyn |
| 4,920,060 A | | 4/1990 | Parrent, Jr. et al. |
| 5,104,621 A | * | 4/1992 | Pfost et al. ................ 422/67 |
| 5,217,590 A | | 6/1993 | Lauer et al. |
| 5,297,431 A | | 3/1994 | White |
| 5,336,467 A | * | 8/1994 | Heidt et al. ............... 422/64 |
| 5,358,613 A | | 10/1994 | Schneider et al. |

(Continued)

*Primary Examiner* — Joseph W Drodge
(74) *Attorney, Agent, or Firm* — Jamie H. Rose (57) ABSTRACT

The present invention is a pressurized fluid sample injector system consisting of a sample needle, multiport valve, sample loop, metering syringe and a pressure assist pump. The speed of sample transport into the sample loop is increased by pressurizing the fluid in the system and metering the sample into the sample loop. The elevated system pressure allows the fluids to be moved faster than the vapor pressure would normally allow in a system at ambient pressure.

33 Claims, 7 Drawing Sheets

U.S. PATENT DOCUMENTS

| | | |
|---|---|---|
| 5,531,959 A | 7/1996 | Johnson et al. |
| 5,578,270 A * | 11/1996 | Reichler et al. .......... 422/67 |
| 5,667,657 A | 9/1997 | Recknor et al. |
| 5,760,299 A | 6/1998 | Johnson et al. |
| 5,814,742 A | 9/1998 | Vissers et al. |
| 6,299,767 B1 | 10/2001 | Dourdeville |
| 6,382,035 B1 * | 5/2002 | Nichols .............. 73/863.72 |
| 2002/0192113 A1 * | 12/2002 | Uffenheimer et al. ...... 422/67 |

* cited by examiner

PRESSURIZED FLUID SAMPLE INJECTOR AND METHOD OF INJECTING FLUID SAMPLES

CROSS REFERENCE TO RELATED APPLICATIONS

This application is a continuation-in-part of U.S. application Ser. No. 11/072,906, filed Mar. 4, 2005, which is a continuation of PCT/US03/28249, designating the U.S. and filed Sep. 10, 2003, which claims benefit of U.S. Provisional Application No. 60/409,836, filed Sep. 11, 2002. The entire contents of these applications are incorporated herein by reference.

STATEMENT ON FEDERALLY SPONSORED RESEARCH

N/A

FIELD OF THE INVENTION

The present invention relates to sample handling and injection systems and in particular to apparatus and methods for increasing the speed of the injection cycle.

BACKGROUND OF THE INVENTION

In one form of liquid chromatography sample injection, a sample is drawn into a needle or capillary and then loaded into a sample loop by pulling the fluid through the needle and any associated tubes into the sample loop. After the sample is in the sample loop, the sample loop is connected to an injection mechanism, such as a pump/detector system, that pushes the sample through a liquid chromatography column where a separation takes place. The sample can be pulled through the system of tubes at a flow rate that is directly related to the vapor pressure of the fluid. If the fluid is drawn through the tubing too quickly, the fluid can vaporize and cause undesirable results in sample integrity as well as sample positioning within the sample loop. This phenomenon forces the sample loading flow rate to remain below the flow rate that will cause vaporization. In most cases this limitation means that sample loading is a significant portion of the overall sample injection cycle time. With screening processes requiring many sample injection cycles, there is impetus to reduce the sample injection cycle. One way to reduce the sample injection cycle, is to speed up the sample loading process.

SUMMARY OF THE INVENTION

In the present invention, sample loading speed is increased significantly by pressurizing the fluid system, thus avoiding vaporization of the fluid. This process allows the sample to be transported through the system faster than in a system that draws the sample into a sample loop without utilizing an elevated pressure. Ultimately, the faster sample loading time reduces the overall cycle time between sample injections.

The invention embodies a pressurized sample injector system, which utilizes elevated pressure to aid sample delivery to a sample loop. In one embodiment, the sample loop is connected across a multiport valve that allows the sample loop to be alternately connected to the sample loading mechanism and the separation mechanism. The sample loading mechanism consists of an aspirating needle, which has already aspirated a sample from a container, that is sealed to a pressure vessel for the loading operation. The aspirating needle is connected to one side of the sample loop through the multiport valve. A metering syringe is connected to the other side of the sample loop through the multiport valve. After the aspirating needle is sealed in the pressure vessel, a pressure assist pump is substantially sealed to the pressure vessel creating a substantially sealed path through the pressure assist pump, the sample loop and the metering syringe.

With the multiport valve in a first position, a sample is aspirated from a container holding the sample into the sample needle. The needle tip is then connected to the pressure vessel and the pressure assist pump and the fluid path is pressurized. The sample is transported from the aspirating needle to the sample loop by creating a pressure differential across the path from the pressure vessel to the metering syringe. After the multiport valve is moved to a second position, the sample is moved from the sample loop to an analytical column by a gradient pump. The second position of the multiport valve disconnects the metering syringe and the aspirating needle from the sample loop and connects the aspirating needle directly to the metering syringe allowing wash cycle(s) to cleanse the flow path while the injection and separation are proceeding.

BRIEF DESCRIPTION OF THE DRAWINGS

The above noted and other features of the invention will be better understood from the following detailed description, when considered in connection with the accompanying drawings, in which.

DETAILED DESCRIPTION

The numerous teachings of the present application will be described with particular reference to the presently preferred embodiment. However, it should be understood that these embodiments provide only a few examples of the advantageous uses of the teachings herein. In general, statements made in the specification of the present application do not necessarily delimit any of the various claimed inventions. It will be obvious to those skilled in the art that various modifications can be made without departing from the spirit and scope of this invention.

Figure 1:
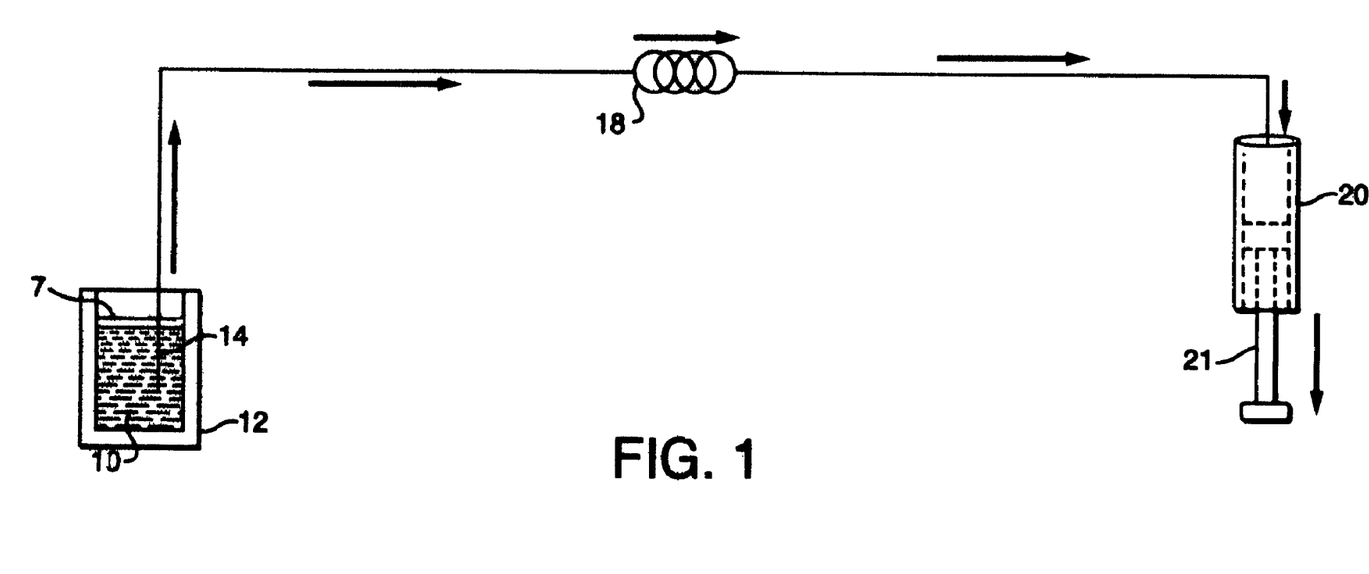
FIG. 1 depicts part of the apparatus.

In FIG. 1 a simplified method of moving a sample quickly is illustrated. A quantity of sample 10 is held in a container 12. A first end of an aspirating needle 14 is in fluid communication with a first end of a sample loop 18 and the second end of the sample loop 18 is in fluid communication with a metering syringe 20. The fluid path from the needle 14 to the syringe 20 is filled with a solute. A second end of the aspirating needle 14 is placed in the sample 10 through a seal 7 that allows the sample 10 to be held under pressure. Once the sample is pressurized, the entire fluid path from the sample 10 to the metering syringe 20 is under pressure.

When the plunger of the metering syringe 20 is pulled back, a pressure differential is established between the metering syringe 20 and the sample 10 which transports the sample liquid through the needle 14 and into the sample loop more swiftly than in a fluidic system that is not under pressure.

In the system as depicted in FIG. 1, there is frequently the need to conserve sample 10 rather than fill the entire fluid path with sample 10. In these cases, after the sample 10 is aspired into the aspirating needle 14, the needle is lifted from the sample 10 and placed in a pressurized bath of fluid (not shown). The fluid then brackets the sample within the fluid path as the sample is loaded into the sample loop 18. The system must adjust the amount of sample used to account for the fact that the fluid and the sample mix at the interface between fluids, but this technique does save sample over the method that fills the entire fluid path with sample.

When the needle is moved between successive sealed baths of fluid, the device of FIG. 1 is useful for loading a sequence of fluids into a lengthy loop. However, the handling of the samples could be simplified, the concentration of the samples can be made consistent and the amount of sample used can be minimized using air gaps between samples and by connecting the sample loop across the ports of a suitably configured multiport valve.

Figure 2A:
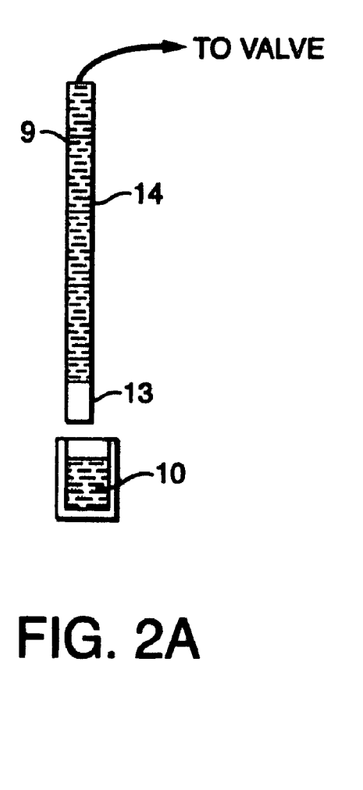
FIG. 2 depicts the steps of sample aspiration.
Figure 2B:
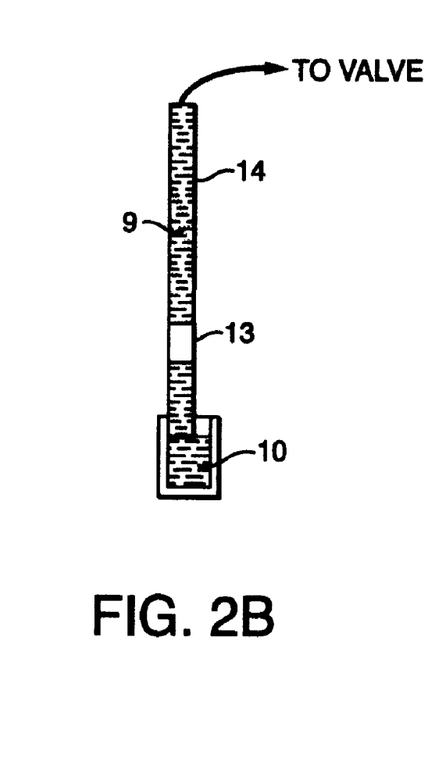
Figure 2C:
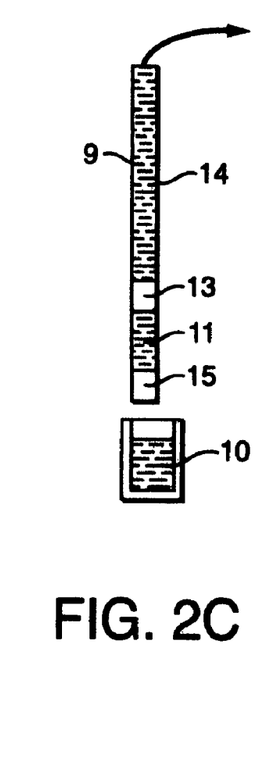

As shown in the embodiment depicted in FIG. 2, in order to minimize dilution of the aspirated metered sample 11, the metered sample 11 is typically bracketed by air gaps within the aspirating needle. The aspirating needle starts filled with fluid 9 and, as shown in FIG. 2A, before aspiration the metering syringe (not shown) is drawn back to pull in a volume of air 13 at the tip of the aspirating needle 14. At 2B, the aspirating needle 14 is placed into the sample 10 and the metering syringe is further pulled back a metered amount which draws a predetermined metered sample portion 11 into the aspirating needle 14. In one embodiment shown at 2C, the aspirating needle 14 is then lifted from the sample 10 and a post-sample air gap 15 is drawn into the aspirating needle 14 by the metering syringe.

Figure 3:
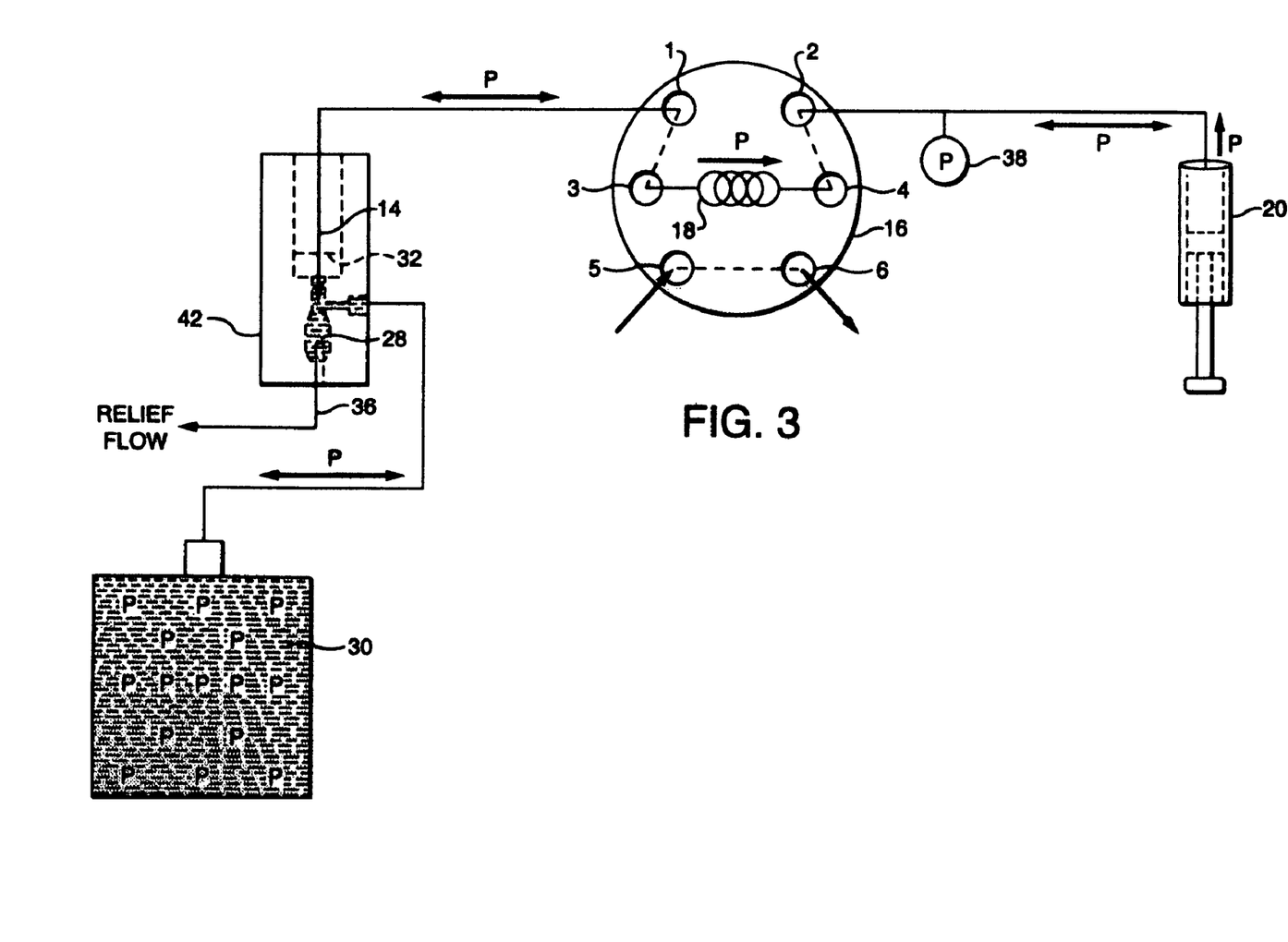
FIG. 3 depicts one embodiment of the apparatus during pressurization.

FIG. 3 depicts an embodiment of the invention showing pressurization of the metered sample 11 while in the aspirating needle 14 and the use of a multiport valve 16. The apparatus is shown after aspiration of the metered sample 11. The aspirating needle 14 containing the metered sample 11 is placed in a pressurized fluid 28 held in a pressure vessel 42 adapted for this purpose. The aspirating needle 14 is sealed to the pressure vessel 42 by seal 32. A pressure assist pump 30 is in fluid communication with the pressure vessel 42 to pressurized fluid 28. With the aspirating needle in the pressurized fluid 28, the entire sample path from the pressurized fluid 28, through the aspirating needle 14, the sample loop 18 and to the metering syringe 20 is pressurized. All of the connections of the present invention substantially seal the sample path from ambient pressure. A relief flow means 36 may be used in conjunction with the pressure assist pump to further regulate the pressure on the pressurized fluid 28. A pressure monitor 38 may be connected to the pressurized fluid line for diagnostic and/or control purposes.

Figure 4:
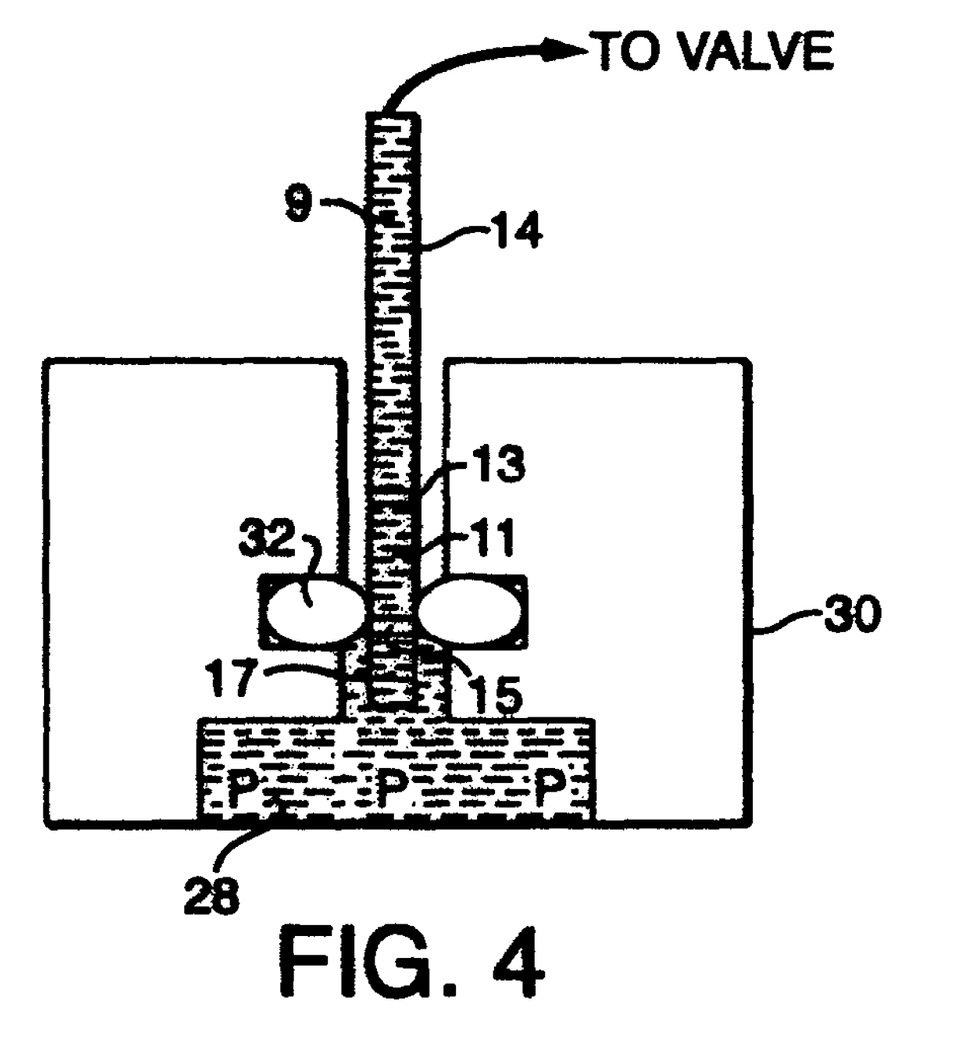
FIG. 4 depicts the pressurization of a sample.

FIG. 4 depicts the metered sample 11, bracketed by air gaps, being pressurized in the aspirating needle 14 before being transported under pressure to the sample loop 18. In one embodiment, the aspirating needle 14 is sealed to the pressure vessel 42 by an O-ring 32. A lip seal or any other means for substantially sealing the aspirating needle 14 to the pressure vessel 42 is appropriate. As the pressure on the pressurized fluid 28 increases, the air gaps 13, 15 are compressed and a quantity 17 of the pressurized fluid 28 is drawn into the aspirating needle 14.

The multiport valve 16 has two positions: in the first position (illustrated in FIG. 3) ports one and three, two and four, and five and six are fluidically connected; in the second position, ports one and two, three and five and four and six are fluidically connected. In one embodiment, the aspirating needle 14 is connected to the first port 1. The sample loop 18 is connected across the multiport valve 16 utilizing ports 3 and 4. The metering syringe 20 is connected to the multiport valve 16 at port 2. In many embodiments, a gradient pump (not shown) is connected to the multiport valve 16 at port 5 and an analytical column (not shown) is connected to the multiport valve 16 at port 6. The multiport valve is adapted to operate up to the pressures being provided by the pressure assist pump and/or the gradient pump. When the multiport valve is in the first position as shown in FIG. 3, the gradient pump and column are maintained in fluid communication by the multiport valve 16 and the aspirating needle 14, sample loop 18 and metering syringe 20 are maintained in fluid communication by the multiport valve 16. The first position is also used to draw the metered sample 11 into the aspirating needle 14 before the transport operation depicted by FIG. 3. In the second position (not shown), the multiport valve 16 maintains the gradient pump, sample loop 18 and analytic column in one fluidic path, while the aspirating needle 14 and metering syringe 20 are maintained in fluid communication in a separate fluidic path. This position allows the gradient pump to push the metered sample 11 from the sample loop 18 onto the analytic column while the rest of the device undergoes a cleaning operation.

The metering syringe 20 is for drawing a metered amount of fluid through the sample path. The metering syringe 20 functions by creating a vacuum in the syringe. The vacuum creates a pressure differential between the aspirating needle 14 and the metering syringe 20 that pulls fluid toward the syringe. By controlling the volume of fluid pulled into the syringe 20, the device controls how far the leading edge of the metered sample 11 moves along the sample path. The metering syringe 20 can be any pump operating on this principle.

Multiport valves having different numbers of ports may be utilized in the device. For instance, a four port valve with two positions could be used to draw the metered sample into a sample loop in one position and isolate the sample loop in the second position. Sample loops so filled could be disconnected and retained for further processing. Control means to position the aspirating needle, control the multiport valve and position the metering syringe are needed to coordinate the components.

Figure 5A:
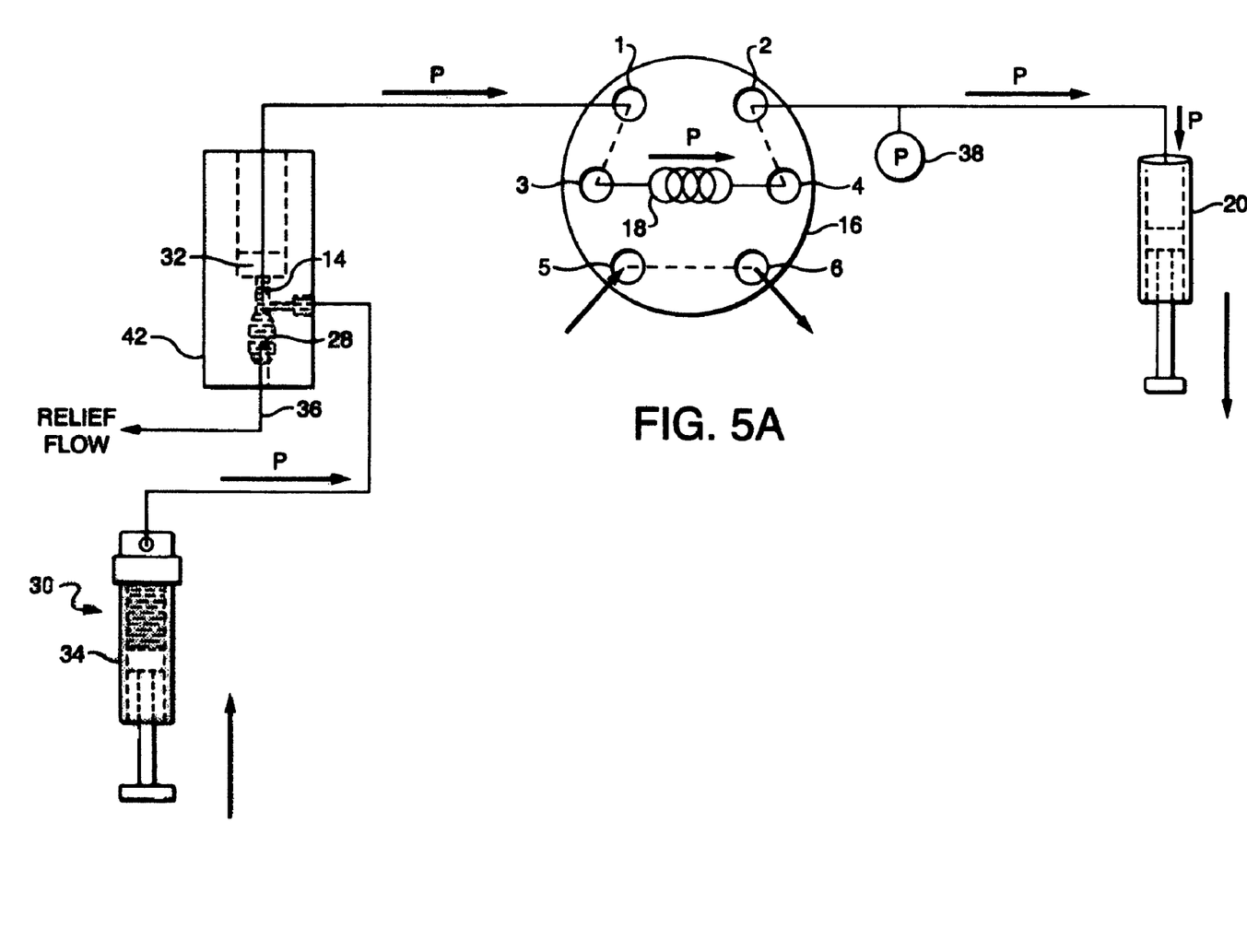
FIG. 5A depicts the apparatus during metering.

In a preferred embodiment shown in FIG. 5A, the pressure assist pump 30 is a wash syringe 34, which may also be used to supply wash fluid for cleansing the sample path. In FIG. 5A, the metering syringe 20 is drawn back creating a pressure differential across the sample path. When the metering syringe 20 is drawn back a calibrated distance, the metered sample 11 is positioned in the sample loop 18, and fluid from the pressurized fluid 28 fills the remainder of the sample path behind the metered sample 11. Since the wash syringe 34 is sealed to the fluid path and has maintained the pressure on the pressurized fluid 28, the metered sample 11 experiences little pressure variation and does not vaporize. Therefore, the metered sample 11 can be moved rapidly into the sample loop 18.

Figure 5B:
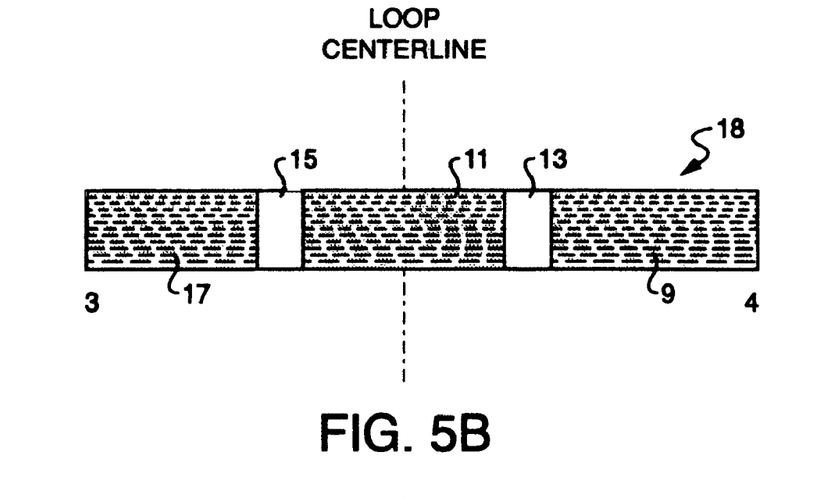
FIG. 5B depicts a partial loop sample in the sample loop after metering.

FIG. 5B illustrates a partial loop placement used to position the metered sample 11 in the sample loop 18 when very small quantities of sample 10 are available. Here the sample loop 18 extends from port 3 to port 4 of the multiport valve 16 and the metered sample 11 is centered in the loop 18. When the metered sample 11 does not fill the sample loop 18, the remainder of the sample loop 18 is occupied by transport fluids 17, 9 and the air gaps 13, 15. Centering the metered sample 11 in a partial loop placement is preferred, but satisfactory result will be obtained as long as the entire metered sample 11 is brought into the sample loop 18. Partial loop placement can assure that a known quantity of sample 10 is used, but the sample will be diluted by the transport fluids in the sample loop 18 and the quantity of air in the air gaps is transferred to the analytical column. Small air gaps are required for partial loop placements to minimize the effects of the air on the analytical column.

Figure 5C:
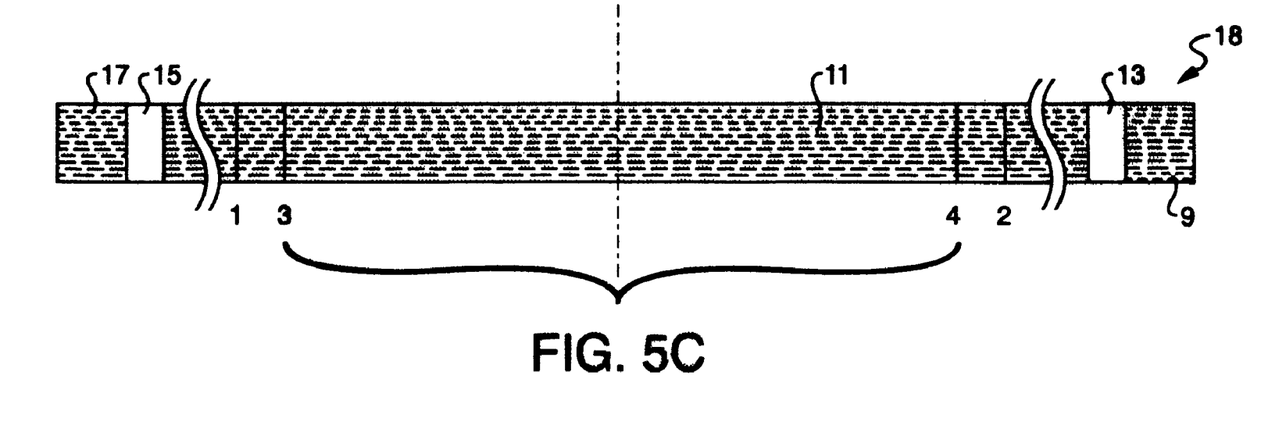
FIG. 5C depicts a full loop sample with overfill in the sample loop after metering.

When sufficient sample 10 is available, the metered sample 11 is positioned using a "full loop with over fill" as illustrated in FIG. 5c. Here, more sample 10 than can be held by the sample loop 18 is drawn into the aspirating needle 14. In one embodiment, when the metering syringe 20 is drawn back, it positions the metered sample 11 centered in the sample loop 18. Because the loop is overfilled, the metered sample 11 not only fills the sample loop 18 but also extends past the sample loop ports 3, 4, and usually past the connection port 1 for the aspirating needle 14 and the connection port 2 for the metering syringe 20. This positioning places the air gaps 13, 15 well beyond the sample loop 18. The advantage of the full loop with over fill is that it assures that a known quantity of full strength sample is injected into the analytical column from the sample loop 18 during the loading phase of the cycle.

In a second embodiment of the full loop with overflow, the metered sample 11 is not centered but rather is positioned with the trailing air gap 15 just before sample loop port 3. This embodiment takes account of the fact that sample near the leading air gap 13 may become diluted due to dispersion. Consistent concentration of sample is optimized by minimizing the amount of possibly diluted sample near the leading air gap 13 that is positioned in the sample loop 18, and maximizing the amount of concentrated sample near the trailing air gap 17 positioned in the sample loop 18.

Since the metered sample 11 is pressurized within the sample path, the metered sample 11 does not vaporize when it is transported into the sample loop 18. Determination of the pressurization level for optimum performance takes the viscosity of the sample and other fluids, the desired positioning speed and the internal diameters (ID) of the sample needle, the interconnecting tubing, the multiport valve, and the metering syringe into account. As an example, in one instance using the parameters listed in Table 1, sample movement speeds of 600-2000 µL/min were attained. This system exhibited a sample load time up to 10 times greater than could be achieved without pressurization. Pressures beyond 150 psig can be used, but the unpressurized air gap size must be increased significantly creating an undesirable effect on cycle time.

TABLE 1

| Sample, fluid filler and wash fluid | 50% Methyl Alcohol (MeOH) and 50% Water (H$_2$0) |
| --- | --- |
| Valve ID | 0.006 in |
| loop ID | 0.016 in |
| aspirating needle ID | 0.010 in |
| sample sizes | 1 µL and 5 µL |
| pressure | 150 psig |
| interconnecting tubing | none |

Figure 6:
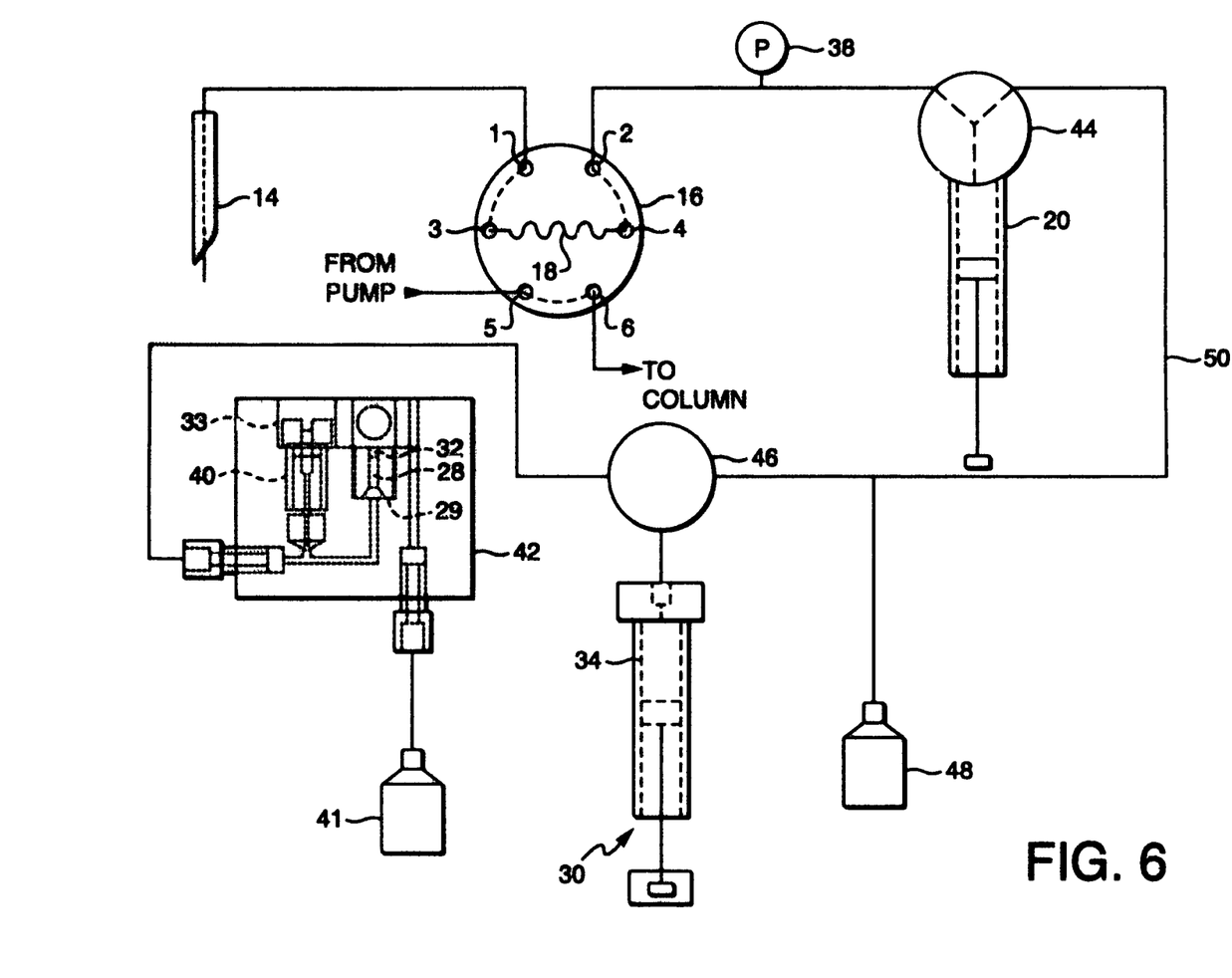
FIG. 6 depicts one embodiment of the invention.

In the preferred embodiment depicted in FIG. 6, the apparatus is set up to operate in a cycle having two phases: one phase transports the metered sample 11 into the sample loop 18 and the second phase cleans the fluid path while the metered sample 11 is being pushed through the analytical column. The cleaning mechanism shown in the figure is representative only, as cleaning technology is well known in the art. A wash syringe pump is used to pressurize the fluid path during the sample transport phase of the cycle. The wash syringe 34, acting as the pressure assist pump 30, maintains a wash block 42, functioning as the pressure vessel, at the desired pressure. A pressure regulating vent 40 is used to maintain a substantially constant pressure while the aspirating needle 14 is in the wash block 42. The wash block 42 is constructed so that excess fluid from the pressure regulating vent and the upper portion of a sealed chamber 29 is directed to a collection area 33 that drains into a waste container 41.

Once the metered sample 11 has been aspirated into the aspirating needle 14, the aspirating needle 14 is inserted in the O-ring 32 of the wash block 42 and the volume of fluid between the metering syringe 20 and the pressure assist pump 30 is pressurized to assist sample movement. Valve 44, at the head of the metering syringe 20, is set to provide connection between the multiport valve 16 and the metering syringe 20 during this part of the cycle. Pressure is created in the system by dispensing fluid from the pressure assist pump 30, here the wash syringe 34, and is held constant by the pressure regulating vent 40. With the system at the operating pressure, the metering syringe 20 meters back a pre-determined volume in order to transport the metered sample 11 from the the aspirating needle 14 into the sample loop 18. After the sample is positioned in the sample loop 18, the multiport valve 16 is actuated and the sample in the sample loop 18 is connected to the gradient pump and analytical column for injection into the analytical column.

Once the sample loop 18 has been removed from the fluid path, the apparatus changes to the cleaning phase. The aspirating needle 14 is withdrawn from the O-ring 32 and held above the collection area 33. Valve 46 changes state to allow the wash syringe to be recharged from a wash reservoir 48. Valve 44 changes state to allow wash fluid to be supplied from wash reservoir 48 to the line connected to multiport valve port 2, through the multiport valve 16 to the aspirating needle 14 where it is flushed into the waste 41. Typically, there is sufficient time to run a number of cycles of cleaning fluid through the fluidic path before the sample loop is reconnected to the apparatus.

The invention allows a sample to be transported into a sample loop in significantly less time than it takes at atmospheric pressure, where transport speed is constrained by the vapor pressure of the fluids transported. Sample positioning accuracy is also improved over other chromatography systems as well. While the above is a description of specific embodiments of the present invention, modifications, alternatives and equivalents may be used while remaining within the scope and spirit of the following claims. Additionally, although the preferred embodiment has been illustrated and described, it will be obvious to those skilled in the art that various modifications can be made without departing from the spirit and scope of this invention. Such modifications are to be considered as included in the following claims unless the claims expressly recite differently.

What is claimed is:
1. A device for loading a sample comprising:
   a. a sample container;
   b. a pressure vessel holding a pressurized fluid, said vessel having an opening for receiving an aspirating needle in sealing engagement and for delivering the pressurized fluid to the needle;
   c. the aspirating needle, which has a passage having a first end and a second end and contains said sample in said passage, said first end for placement in said sample container, to aspirate said sample from said sample container into said passage, and for placement in said pres- sure vessel to allow said pressurized fluid from the pressure vessel to enter said passage to displace said sample within said passage;

d. a sample loop having a first loop end and a second loop end, said first loop end in fluid communication with said second end of said passage of said aspirating needle, said sample loop for receiving said sample from said passage of said aspirating needle and for containing said sample;

e. a metering syringe in fluid communication with said second loop end of said sample loop for creating a pressure differential between said pressure vessel and said metering syringe to draw said sample from said passage of said needle and into said sample loop; and f. a pressure source for placing said pressure vessel under pressure, to cooperate with the metering syringe to create said pressure differential and to deliver the pressurized fluid to the needle to facilitate movement of said sample in said passage out of said second end of said aspirating needle and into said sample loop, wherein said pressure source comprises a pressure assist pump sealed to a fluid path communicating said pressure source to said pressure vessel and adapted to maintain pressure and minimize pressure variation of said pressurized fluid so that said sample aspirated from said sample container does not vaporize.

2. The device of claim 1 further comprising a control means for controlling movement of said aspirating needle.

3. The device of claim 1 further comprising a control means for controlling said pressure in said pressure source.

4. The device of claim 1 further comprising a control means for controlling said metering syringe to draw said sample into said aspirating needle and to draw said sample from said aspirating needle to said sample loop.

5. The device of claim 4 further comprising said control means for coordinating controlling of said metering syringe and at least one of controlling of said pressure in said pressure source and controlling movement of said aspirating needle.

6. The device of claim 1 further comprising:

a multiport valve having at least a first port, a second port, a third port, and a fourth port and capable of assuming a first position and a second position, said first port in fluid communication with said second end of said aspirating needle, said second port in fluid communication with said first loop end of said sample loop, said third port in fluid communication with said second loop end of said sample loop, and said fourth port in fluid communication with said metering syringe, wherein said multiport valve in said first position forms a load path from said aspirating needle, through said sample loop to said metering syringe for transporting said sample; and said multiport valve in said second position isolates said sample loop from said aspirating needle and metering syringe for retaining said sample.

7. The device of claim 6 further comprising a control means to control said positioning of said multiport valve.

8. The device of claim 7 further comprising said control means to coordinate said positioning of said multiport valve and at least one of controlling movement of said aspirating needle, controlling said pressure in said pressure source, and controlling said metering syringe to draw said sample into said aspirating needle and to draw said sample from said aspirating needle to said sample loop.

9. The device of claim 6 wherein said multiport valve in said second position further forms a wash path from said metering syringe, through said multiport valve to said aspirating needle for cleaning operations.

10. The device of claim 6 wherein said multiport valve further comprises:

a fifth port for fluid communication with a pump; and a sixth port for fluid communication with an analytical column;

wherein said multiport valve in said second position has an injection fluid path from said pump, through said sample loop to said analytical column for injecting said sample onto said analytical column.

11. The device of claim 10 wherein said multiport valve in said first position has an elution fluid path from said pump to said analytical column for performing elution operations.

12. The device as in claim 6 wherein, said multiport valve is a high pressure injector valve.

13. The device as in claim 6 further comprising, a pressure transducer for monitoring pressure between said multiport valve and said metering syringe.

14. A device for loading a sample comprising:

a. a sample container;

b. a pressure vessel holding a pressurized fluid, said vessel having an opening for receiving an aspirating needle in sealing engagement and for delivering the pressurized fluid to the needle;

c. the aspirating needle, which has a passage having a first end and a second end and contains said sample in said passage, said first end for placement in said sample container, to aspirate said sample from said sample container into said passage, and for placement in said pressure vessel to allow said pressurized fluid from the pressure vessel to enter said passage to displace said sample within said passage;

d. a sample loop having a first loop end and a second loop end, said first loop end in fluid communication with said second end of said passage of said aspirating needle, said sample loop for receiving said sample from said passage of said aspirating needle and for containing said sample;

e. a metering syringe in fluid communication with said second loop end of said sample loop for creating a pressure differential between said pressure vessel and said metering syringe to draw said sample from said passage of said needle and into said sample loop; and f. a pressure source for placing said pressure vessel under pressure, to cooperate with the metering syringe to create said pressure differential and to deliver the pressurized fluid to the needle to facilitate movement of said sample in said passage out of said second end of said aspirating needle and into said sample loop, wherein said pressure source is a wash syringe in fluid communication with said pressure vessel.

15. The device as in claim 14 further comprising, a wash system between said wash syringe and said metering syringe.

16. A device for moving a sample using a volume of fluid comprising:

a. a pressure vessel, said vessel having an opening for receiving an aspirating needle in sealing engagement;

b. an aspirating needle having a passage having a first end and a second end and containing said sample in said passage, said first end for placement in said pressure vessel to allow fluid to enter said passage to displace said sample within said passage, and said second end for being placed in fluid communication with a sample loop;

c. a sample loop having a first loop end and a second loop end, said first loop end in fluid communication with said aspirating needle and said second loop end in fluid communication with a metering syringe, said sample loop for receiving said sample from said aspirating needle and for containing said sample;

d. a metering syringe in fluid communication with said second loop end of said sample loop for creating a pressure differential between said pressure vessel and said metering syringe to draw said sample from said needle and into said sample loop; and e. a pressure source for placing said pressure vessel under pressure, to facilitate movement of said sample out of said second end of said aspirating needle, wherein said pressure source is a wash syringe in fluid communication with said pressure vessel further comprising, a wash system between said wash syringe and said metering syringe wherein said wash system comprises:

a wash fluid source;

an alpha valve means, having at least three ports and capable of assuming two positions, in fluid communication with said metering syringe, said wash fluid source and said fourth port of said multiport valve, wherein said alpha valve means is in said first alpha valve position when said multiport valve is in said first position and is in said second alpha valve position when said multiport valve is in said second position; said first alpha valve position for connecting said fourth port and said metering syringe, and said second alpha valve position for placing said wash fluid source in fluid communication with said metering syringe and said fourth port to direct a wash fluid through said wash path to effect cleaning of said wash path; and a beta valve means, having at least three ports and capable of assuming two positions, in fluid communication with said pressure source, said wash fluid source and said wash syringe, wherein said beta valve means is in said first beta valve position when said multiport valve is in said first position and said beta valve means is in said second position when said multiport valve is in said second position; said first beta valve position for connecting said wash syringe to said pressure source for maintaining pressure and said second beta valve position for connecting said wash syringe to said wash fluid source for refilling said wash syringe.

17. The device of claim 16 further comprising control means for controlling said position of said alpha valve and for controlling said position of said beta valve so that said alpha valve and said beta valve are respectively in said first position simultaneously and said alpha valve and said beta valve are respectively in said second position simultaneously, said control means further for coordinating positioning of said alpha valve and said beta valve with the positioning of said multiport valve.

18. The device of claim 17 wherein said control means further coordinates said positioning of said alpha valve and said beta valve with at least one of controlling movement of said aspirating needle, controlling positioning of said multiport valve, controlling said pressure in said pressure source, and controlling said metering syringe to draw said sample into said aspirating needle and to draw said sample from said aspirating needle to said sample loop.

19. A device for loading a sample from a sample container comprising:

a. a sample container;

b. a pressure vessel holding a pressurized fluid, said vessel having an opening for receiving an aspirating needle in sealing engagement and for delivering the pressurized fluid to the needle;

c. the aspirating needle, which has a passage having a first end and a second end and contains said sample in said passage, said first end for placement in said sample container, to aspirate said sample from said sample container into said passage, and for placement in said pressure vessel to allow said pressurized fluid from the pressure vessel to enter said passage to displace said sample within said passage;

d. a sample loop having a first loop end and a second loop end, said first loop end in fluid communication with said second end of said passage of said aspirating needle, said sample loop for receiving said sample from said passage of said aspirating needle and for containing said sample;

e. a metering syringe in fluid communication with said second loop end of said sample loop for creating a pressure differential between said pressure vessel and said metering syringe to draw said sample from said passage of said needle and into said sample loop; and f. a pressure source for placing said pressure vessel under pressure, to cooperate with the metering syringe to create said pressure differential and to deliver the pressurized fluid to the needle to facilitate movement of said sample in said passage out of said second end of said aspirating needle and into said sample loop, wherein, said pressure source is a pressure assist pump having a relief flow means.

20. The device as in claim 19 further comprising, a pressure regulating vent, functioning as said relief flow means, in said pressure source for holding said pressure in said device substantially constant.

21. The device as in claim 1 further comprising, an O-ring in said pressure vessel to substantially seal said opening to said aspirating needle.

22. The device as in claim 1 further comprising, a lip seal in said pressure vessel to substantially seal said opening to said aspirating needle.

23. The device as in claim 1 wherein said sample in said aspirating needle is bracketed by air gaps before said first end of said aspirating needle is sealed with said pressure vessel.

24. The device as in claim 1 wherein said pressure differential is created by withdrawing said metering syringe a predetermined distance that displaces a known volume of fluid, said volume of fluid sufficient to position said sample centered in said sample loop.

25. A method of transferring a sample from a sample container to a sample loop comprising:

forming a sample path comprising an aspirating needle in fluid communication with said sample loop and a metering syringe;

aspirating a sample from said sample container into said aspirating needle by withdrawing said metering syringe a distance;

sealing said aspirating needle to a pressure vessel after aspirating the sample from said sample container;

pressurizing said pressure vessel to a predetermined pressure with a pressure source to pressurize said sample path; and withdrawing said metering syringe a predetermined distance to transport said aspirated sample into said sample loop powered by a pressure differential across said sample path created by said pressure vessel and said metering syringe.

26. The method of claim 25 further comprising placing said sample on an analytical column, comprising:

disengaging said sample loop from said sample path;

connecting said sample loop to a pump at a first end and to said analytical column at a second end; and moving said sample from said sample loop to said analytical column by activating said pump.

27. The method of claim 26 wherein a multiport valve having a plurality of ports and two positions is connected with a first port connected to said sample needle, a second port connected to said a first end of said sample loop, a third port connected to a second end of said sample loop, a fourth port connected to said metering syringe, a fifth port connected to said pump and a sixth port connected to said analytical column, wherein said multiport valve in a first position forms a load path from said sample needle, through the sample loop to the metering syringe, and an elution path from said pump to said analytical column, and wherein said multiport valve in a second position forms a wash path from the aspirating needle to the metering syringe and an injection path from said pump, through said sample loop to said analytical column, the method further comprising:
  performing said aspirating step with said multiport valve in said first position; and
  performing said disengaging and connecting steps by switching said multiport valve from said first position to said second position.

28. The method of claim 27 wherein a control means adapted to control the position of said multiport valve is utilized, said method further comprising:
  forming said sample path by controlling said multiport valve to be in said first position; and
  disengaging said sample loop from said sample path by controlling said multiport valve to be in said second position.

29. The method of claim 28 wherein said control means further coordinates the positioning of said multiport valve with at least one of controlling the positioning of said metering syringe and controlling the positioning of said aspirating needle.

30. The method of claim 25 further comprising:
  maintaining said pressure in said sample path constant utilizing a pressure regulating vent in conjunction with a pressure assisted pump that pressurizes the pressure vessel.

31. The method of claim 25 wherein a control means adapted to control the position of said aspirating needle is utilized, said method further comprising:
  preceding said aspirating step with a step of controlling the position of said aspirating needle to place said aspirating needle in said container; and
  preceding said sealing step with a step of controlling said position of said aspirating needle to remove said aspirating needle from said container and position said aspirating needle in said pressure vessel.

32. The method of claim 25 wherein a control means adapted to control the position of said metering syringe is utilized, said method further comprising:
  performing said aspirating step by controlling the positioning of said metering syringe to withdraw said metering syringe a distance;
  performing said withdrawing step by controlling the positioning of said metering syringe to withdraw said metering syringe a predetermined distance.

33. The method of claim 32 wherein said control means further coordinates controlling the positioning of said metering syringe and controlling the positioning said aspirating needle.

* * * * *